United States Patent
Chodkowski

(10) Patent No.: US 10,881,825 B2
(45) Date of Patent: Jan. 5, 2021

(54) SEALING CUSHION FOR A PATIENT INTERFACE DEVICE THAT HAS A CUSTOM CUSHION SUPPORT ASSEMBLY

(71) Applicant: KONINKLIJKE PHILIPS N.V., Eindhoven (NL)

(72) Inventor: Lauren Patricia Chodkowski, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 221 days.

(21) Appl. No.: 15/539,364

(22) PCT Filed: Dec. 15, 2015

(86) PCT No.: PCT/IB2015/059605
§ 371 (c)(1),
(2) Date: Jun. 23, 2017

(87) PCT Pub. No.: WO2016/108116
PCT Pub. Date: Jul. 7, 2016

(65) Prior Publication Data
US 2018/0264218 A1 Sep. 20, 2018

Related U.S. Application Data

(60) Provisional application No. 62/097,808, filed on Dec. 30, 2014.

(51) Int. Cl.
*A61M 16/06* (2006.01)

(52) U.S. Cl.
CPC ........ *A61M 16/0605* (2014.02); *A61M 16/06* (2013.01); *A61M 16/0666* (2013.01);
(Continued)

(58) Field of Classification Search
CPC .............. A61M 16/0605; A61M 16/06; A61M 16/0683; A61M 16/0666; A61M 16/0622; A61M 2207/10; A61M 2016/0661
See application file for complete search history.

(56) References Cited

U.S. PATENT DOCUMENTS 7,210,481 B1 * 5/2007 Lovell ................... A61M 16/06
128/205.25
8,286,636 B2 10/2012 Darkin et al.
(Continued)

FOREIGN PATENT DOCUMENTS

CN 1750854 A 3/2006
DE 202010011334 U1 10/2010
(Continued)

OTHER PUBLICATIONS

"Ventlab Cannula CPAP Mask Nasal Interface System", 2014 http://www.cpapsupplyusa.com/Ventlab-Nasal-Cannula-System-CS9000.aspx.

*Primary Examiner* — Timothy A Stanis
*Assistant Examiner* — Thao Tran
(74) *Attorney, Agent, or Firm* — Michael W. Haas

(57) ABSTRACT

A patient interface device (8) structured to engage a patient's sub-nasal area is provided and includes a body (22), a cushion (50) and a custom cushion support assembly (100). Patient interface device body includes a sidewall (27) with an upper side (32) including a number of passages (40). Cushion includes a resilient body (52). Cushion body is disposed on patient interface device body. Patient interface device cushion body includes an engagement portion (60) structured to engage a patient's sub-nasal area, and a pocket (70) disposed under cushion body engagement portion. Custom cushion support assembly includes a body (102) with an upper surface (104) including a custom contour (110). Custom cushion support assembly body is disposed in
(Continued)

patient interface device cushion body pocket. In this configuration, custom contour deforms patient interface device cushion body engagement portion to correspond to patient's sub-nasal area.

10 Claims, 7 Drawing Sheets

(52) U.S. Cl.
 CPC . *A61M 16/0683* (2013.01); *A61M 2016/0661* (2013.01); *A61M 2207/00* (2013.01); *A61M 2207/10* (2013.01); *A61M 2210/0618* (2013.01)

(56) References Cited

U.S. PATENT DOCUMENTS

| | | | | |
|---|---|---|---|---|
| 2004/0226566 A1* | 11/2004 | Gunaratnam | ..... | A61M 16/0816 128/207.18 |
| 2005/0205096 A1* | 9/2005 | Matula, Jr. | ........ | A61M 16/0694 128/207.11 |
| 2008/0047560 A1* | 2/2008 | Veliss | ................ | A61M 16/0605 128/206.24 |
| 2010/0000534 A1* | 1/2010 | Kooij | ................ | A61M 16/0616 128/204.18 |
| 2012/0080035 A1 | 4/2012 | Guney | | |
| 2012/0305003 A1 | 12/2012 | Mark | | |
| 2013/0263858 A1* | 10/2013 | Ho | .................... | A61M 16/0683 128/205.25 |
| 2014/0123981 A1* | 5/2014 | Willard | ............. | A61M 16/0633 128/205.25 |
| 2014/0326243 A1* | 11/2014 | Znamenskiy | ..... | A61M 16/0633 128/205.25 |
| 2014/0326246 A1* | 11/2014 | Chodkowski | ......... | A61M 16/06 128/206.24 |
| 2016/0001029 A1* | 1/2016 | Bayer | ................ | A61M 16/0611 128/206.24 |
| 2017/0326320 A1* | 11/2017 | Baigent | ............. | A61M 16/0683 |

FOREIGN PATENT DOCUMENTS

| | | | | |
|---|---|---|---|---|
| WO | WO-2013001438 A1 * | 1/2013 | ............ | A61M 16/06 |
| WO | WO-2013068950 A1 * | 5/2013 | ........ | A61M 16/0057 |
| WO | WO2013068950 A1 | 5/2013 | | |
| WO | WO-2013084109 A1 * | 6/2013 | ........ | A61M 16/0611 |
| WO | WO2013084110 A1 | 6/2013 | | |
| WO | WO2013098727 A2 | 7/2013 | | |
| WO | WO2014013371 A1 | 1/2014 | | |
| WO | WO2014024086 A1 | 2/2014 | | |
| WO | WO2014091370 A1 | 6/2014 | | |
| WO | WO2014141029 A1 | 9/2014 | | |

* cited by examiner

SEALING CUSHION FOR A PATIENT INTERFACE DEVICE THAT HAS A CUSTOM CUSHION SUPPORT ASSEMBLY

This patent application claims the priority benefit under 35 U.S.C. § 371 of international patent application no. PCT/IB2015/059605, filed Dec. 15, 2015, which claims the priority benefit under 35 U.S.C. § 119(e) of U.S. Provisional Application No. 62/097,808 filed on Dec. 30, 2014, the contents of which are herein incorporated by reference.

BACKGROUND OF THE INVENTION

1. Field of the Invention

The present invention pertains to patient interface devices structured to deliver a flow of breathing gas to a user, and, in particular, to a cradle style sealing cushion for a patient interface device that has a custom cushion support assembly.

2. Description of the Related Art

There are numerous situations where it is necessary or desirable to deliver a flow of breathing gas non-invasively to the airway of a patient, i.e., without intubating the patient or surgically inserting a tracheal tube into the patient's esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible sealing cushion on the face of a patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

One type of known patient interface device is called a cradle style patient interface device. A cradle style patient interface device is structured to rest beneath the patient's nose and provides an air-tight seal against the surfaces of the nasal septum and nostrils (and also possibly the upper lip). One major disadvantage of current cradle style sealing cushions is that the seal between the cushion and the nose is very sensitive to the alignment of the cushion to the nose. For this reason, many wearers find it difficult to maintain a reliable seal when using a mask with a cradle style sealing cushion due to misalignment caused by movement of the wearer or external forces acting on the mask (e.g., from a bed pillow). When the seal is broken, the ability of the respiratory therapy device to deliver adequate airflow to the wearer may be compromised. Additionally, air leakage may be directed into the wearer's face, causing discomfort.

SUMMARY OF THE INVENTION

Accordingly, it is an object of the present invention to provide a cradle style patient interface device that overcomes the shortcomings of conventional cradle style patient interface devices. This object is achieved according to one embodiment of the present invention by providing a cradle style patient interface device that includes a custom cushion support assembly that allows a cushion to provide a more complete seal.

In one exemplary embodiment, a patient interface device structured to engage a patient's sub-nasal area includes a body, a cushion and a custom cushion support assembly. Patient interface device body includes a sidewall. Patient interface device body sidewall defines a chamber. Patient interface device body sidewall includes an upper side. Patient interface device body sidewall upper side includes a number of passages. Cushion includes a resilient body. Cushion body is disposed on patient interface device body. Patient interface device cushion body includes an engagement portion structured to engage a patient's sub-nasal area, and, a pocket disposed under cushion body engagement portion. Patient interface device cushion body engagement portion includes a number of passages. Custom cushion support assembly includes a body. Custom cushion support assembly body includes an upper surface defining a number of passages. Custom cushion support assembly body upper surface includes a custom contour. Custom cushion support assembly body is disposed in patient interface device cushion body pocket with each custom cushion support assembly body passage aligned with a patient interface device cushion body engagement portion passage. In this configuration, custom cushion support assembly body upper surface custom contour deforms patient interface device cushion body engagement portion to correspond to patient's sub-nasal area.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
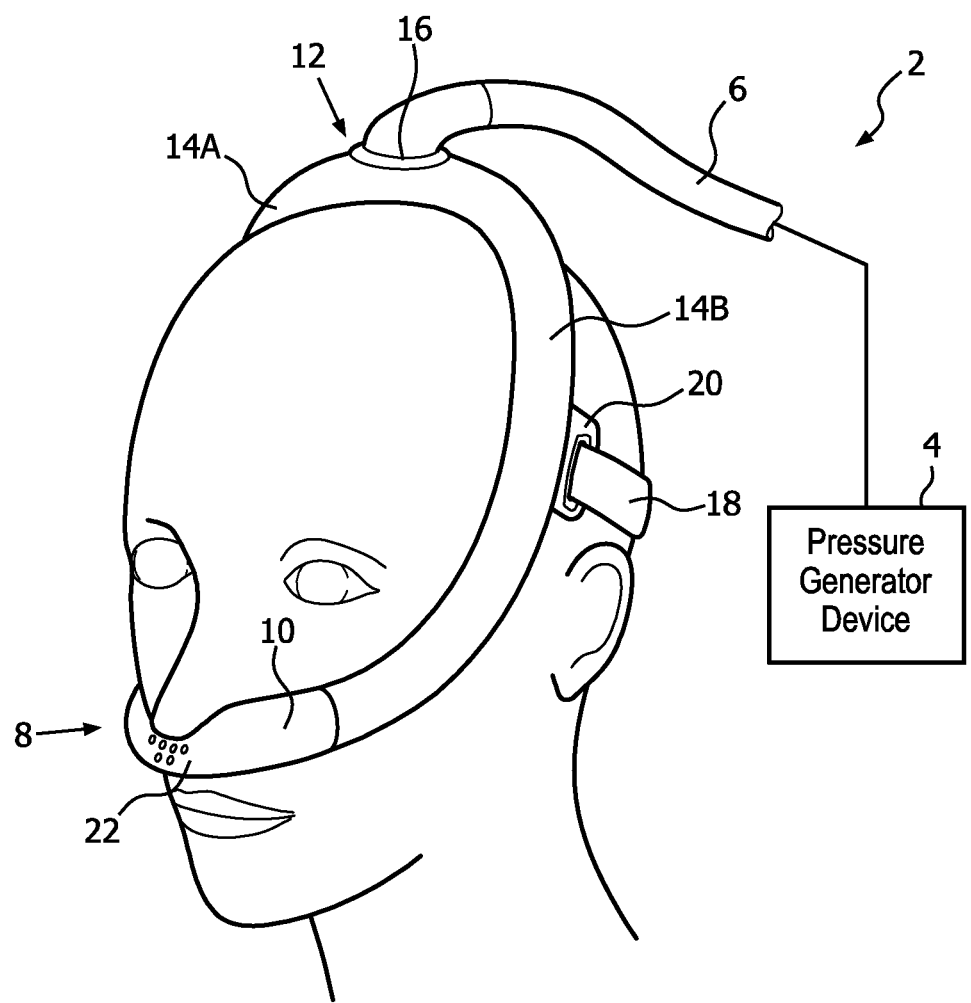
FIG. 1 is a schematic diagram of a system adapted to provide a regimen of respiratory therapy to a patient according to one exemplary embodiment of the invention.

As used herein, the singular form of "a," "an," and "the" include plural references unless the context clearly dictates otherwise. As used herein, the statement that two or more parts or components are "coupled" means that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. Accordingly, when two elements are coupled, all portions of those elements are coupled. A description, however, of a specific portion of a first element being coupled to a second element, e.g., an axle first end being coupled to a first wheel, means that the specific portion of the first element is disposed closer to the second element than the other portions thereof.

As used herein, the statement that two or more parts or components "engage" one another means that the parts exert a force against one another either directly or through one or more intermediate parts or components. As used herein, the word "unitary" means a component is created as a single piece or unit. That is, a component that includes pieces that are created separately and then coupled together as a unit is not a "unitary" component or body. As used herein, the term "number" means one or an integer greater than one (i.e., a plurality).

As used herein, a "coupling assembly" includes two or more couplings or coupling components. The components of a coupling or coupling assembly are generally not part of the same element or other component. As such, the components of a "coupling assembly" may not be described at the same time in the following description.

As used herein, a "coupling" or "coupling component(s)" is one or more component(s) of a coupling assembly. That is, a coupling assembly includes at least two components that are structured to be coupled together. It is understood that the components of a coupling assembly are compatible with each other. For example, in a coupling assembly, if one coupling component is a snap socket, the other coupling component is a snap plug, or, if one coupling component is a bolt, then the other coupling component is a nut. As another example, the portions of two elements that are adhered to each other are a "coupling" or "coupling component(s)." Further, a "coupling" or "coupling component" may include an opening or passage through which another coupling passes.

As used herein, "operatively coupled" means that a number of elements or assemblies, each of which is movable between a first position and a second position, or a first configuration and a second configuration, are coupled so that as the first element moves from one position/configuration to the other, the second element moves between positions/configurations as well. It is noted that a first element may be "operatively coupled" to another without the opposite being true.

As used herein, "correspond" indicates that two structural components are sized and shaped to be similar to each other and may be coupled with a minimum amount of friction. Thus, an opening which "corresponds" to a member is sized slightly larger than the member so that the member may pass through the opening with a minimum amount of friction. This definition is modified if the two components are said to fit "snugly" together. In that situation, the difference between the size of the components is even smaller whereby the amount of friction increases. If the element defining the opening and/or the component inserted into the opening are made from a deformable or compressible material, the opening may even be slightly smaller than the component being inserted into the opening. With regard to surfaces, shapes, and lines, two, or more, "corresponding" surfaces, shapes, or lines have generally the same size, shape, and contours.

As used herein, "a generally continuous seal" may have a gap or may gap when the patient moves. As used herein, "a more complete seal" has a gap that is shorter in length than a gap of a generally continuous seal, or, is resistant to gapping when the patient moves. As used herein, a "longitudinal axis" is not required to be a generally straight line. That is, a "longitudinal axis" as used herein is generally a centerline of a body which can include curves.

As used herein, the term "fabric" means a material consisting of a network of interlaced or otherwise entangled natural or artificial fibers made by, for example and without limitation, weaving, knitting, spreading, crocheting, or bonding (e.g., by chemical, mechanical, heat or solvent treatment) the fibers to form the network, and may include, for example, and without limitation, woven and nonwoven materials. As used herein, a patient's "upper lip" includes the area between the vermilion border and the nose.

As used herein, a patient's "sub-nasal area" includes any of the areas of a patient's body extending about, i.e. around, the nares, the septum between the nares, the septum near the tip of the nose, the transitional area between the nose and upper lip, and the upper lip. The "sub-nasal area" includes epidermis that faces generally downward. Further, it is understood that each human is unique; thus, the exact dimensions of the "sub-nasal area" varies from person to person and may include more or less epidermis in any stated area. For example, for some patients the area of the upper lip in the "sub-nasal area" may be negligible.

As used herein, a patient's "full sub-nasal area" includes all the areas of a patient's body extending about, i.e. around, the nares, the septum between the nares, the septum near the tip of the nose, the transitional area between the nose and upper lip, and the upper lip. As before, it is understood that each human is unique; thus, the exact dimensions of the "full sub-nasal area" varies from person to person and may include more or less epidermis in any stated area.

As used herein, a patient's "peripheral sub-nasal area" includes the area of a patient's body extending about, i.e. around, the nares, the septum near the tip of the nose, the transitional area between the nose and upper lip, and the upper lip. That is, a patient's "peripheral sub-nasal area" extends about the nares. As before, it is understood that each human is unique; thus, the exact dimensions of the "peripheral sub-nasal area" varies from person to person and may include more or less epidermis in any stated area.

As used herein, a patient's "inner sub-nasal area" includes the area inside the nasal cavity at, and adjacent, the flares. The "inner sub-nasal area" includes epidermis disposed within the nasal cavity and that extends generally vertically.

As used herein, a "pocket" means two closely spaced, generally planar surfaces structured to enclose a portion of another component. As used herein, "closely spaced" means that the distance between the planar elements is not greater than five times the thickness of the planar elements. The generally planar surfaces do not have to extend over the area defined by the surface perimeter. That is, unlike, for example, pockets on pants wherein the fabric defining the pocket extends over the area defined by the fabric perimeter, as used herein, a "pocket" may include a number of passages through the planar surfaces so long as a portion of the planar surfaces enclose a portion of another component. By way of a non-limiting example, two U-shaped planar members disposed in a spaced, mirroring orientation define a "pocket."

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 2 adapted to provide a regimen of respiratory therapy to a patient according to one exemplary embodiment of the invention is generally shown in FIG. 1. System 2 includes a pressure generating device 4, a delivery conduit 6, and a patient interface device 8. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8.

In the exemplary embodiment, patient interface device 8 comprises a cradle style nasal mask structured to engage the nose of the patient and provide a seal against the surfaces of the nasal septum and nostrils (and possibly the portion of the patient's mouth above the upper lip), i.e. the sub-nasal area, as described in detail herein. In the present embodiment, patient interface device 8 is a cradle style patient interface device 10 coupled to a tubing assembly 12. As seen in FIG. 1, tubing assembly 12 includes a first arm 14A structured to rest along a first side of the patient's head and a second arm 14B structured to rest along a second side of the patient's head when patient interface device 8 is donned by the patient. A first end of first arm 14A and a first end of second arm 14B are each in fluid communication with cradle style patient interface device 10. In addition, a second end of first arm 14A and a second end of second arm 14B are each in fluid communication with a coupling connector 16 structured to rest on top of the head of the patient when patient interface device 8 is donned by the patient. Delivery conduit 6 is in fluid communication with coupling connector 16 and thereby allows a flow of breathing gas from pressure generating device 4 to be communicated to cradle style patient interface device 10 through tubing assembly 12, and then, to the airway of a patient. In an exemplary embodiment, straps 18 of a headgear component are attached to first arm 14A and second arm 14B via attachment members 20 to secure patient interface device 8 to the patient's head.

Figure 2:
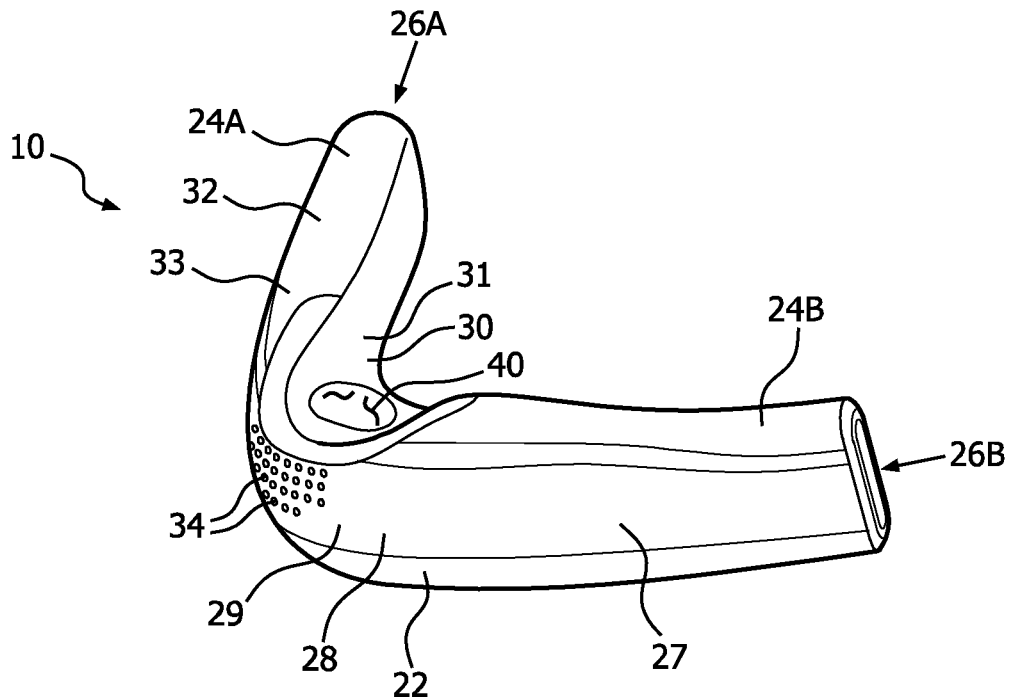
FIG. 2 is a front isometric view.
Figure 3:
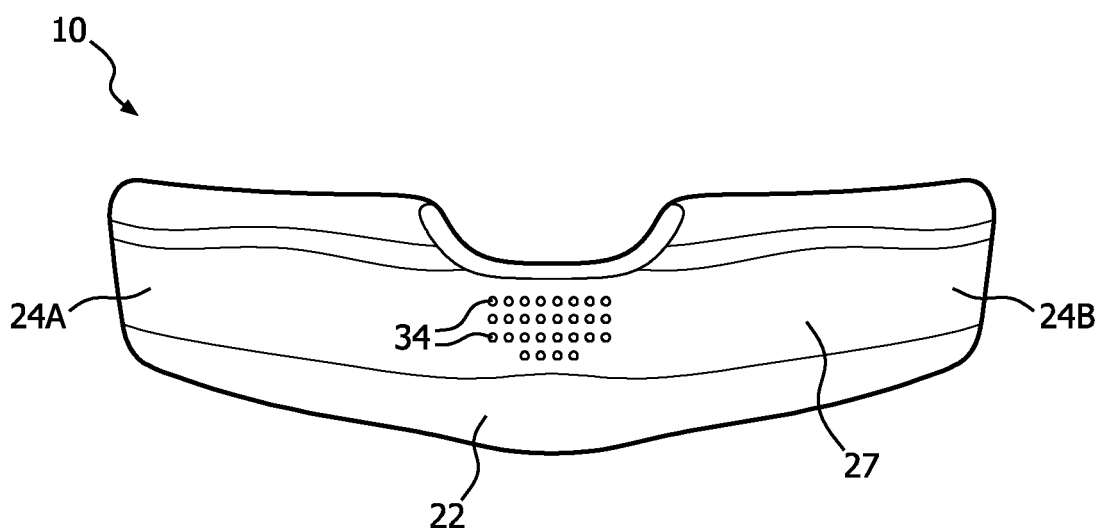
FIG. 3 is a front elevational view.
Figure 4:
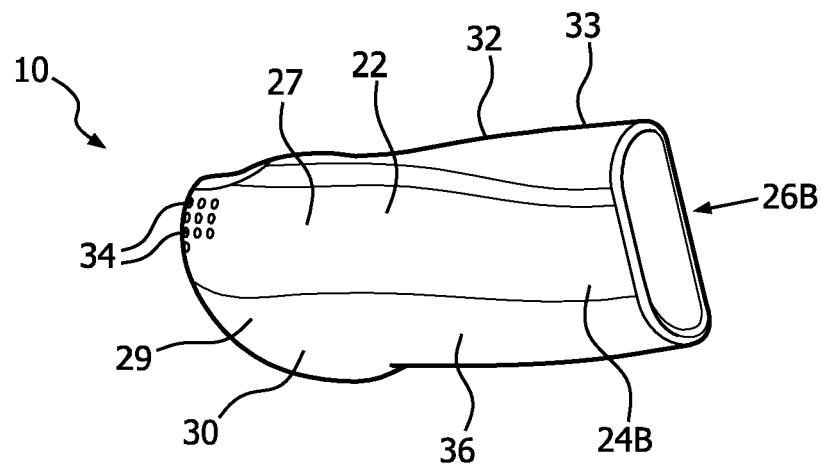
FIG. 4 is a side elevational view.
Figure 5:
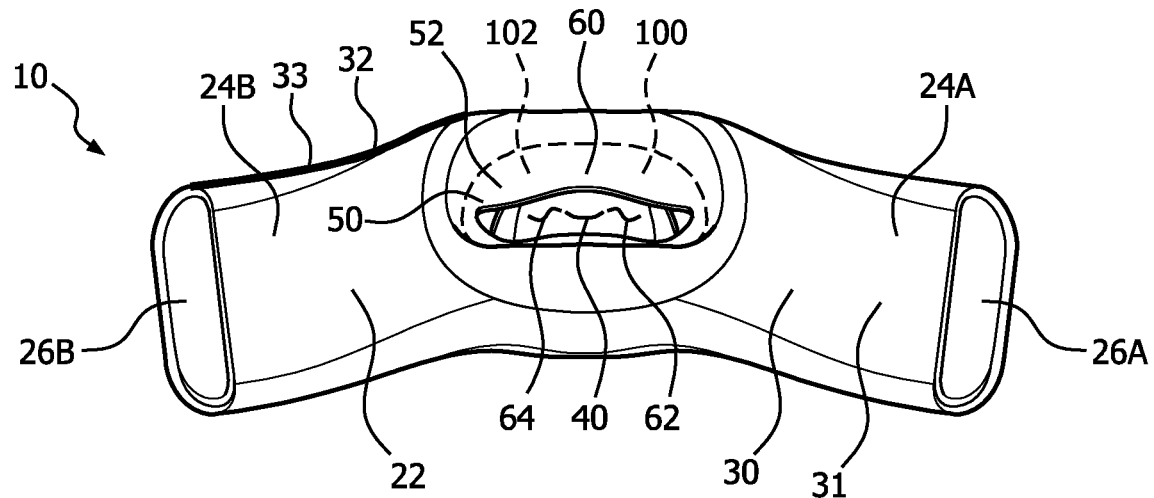
FIG. 5 is a rear elevational view.
Figure 6:
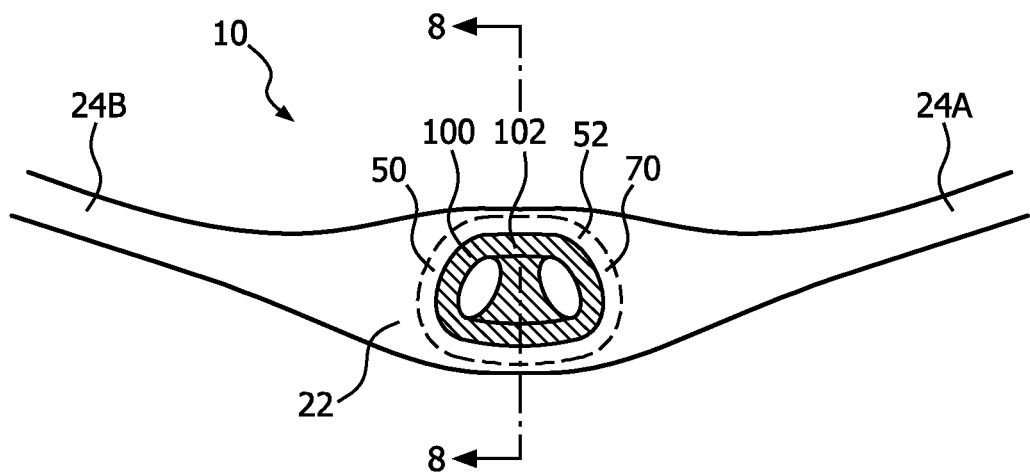
FIG. 6 is a top plan view of a cradle style sealing cushion according to an exemplary embodiment of the present invention that may be employed in a patient interface device of the system of FIG. 1.
Figure 7:
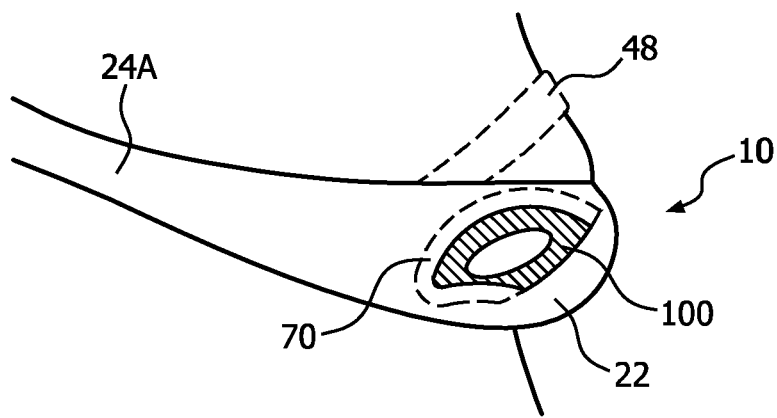
FIG. 7 is a schematic diagram of a system adapted to provide a regimen of respiratory therapy to a patient according to another exemplary embodiment of the invention.
Figure 8:
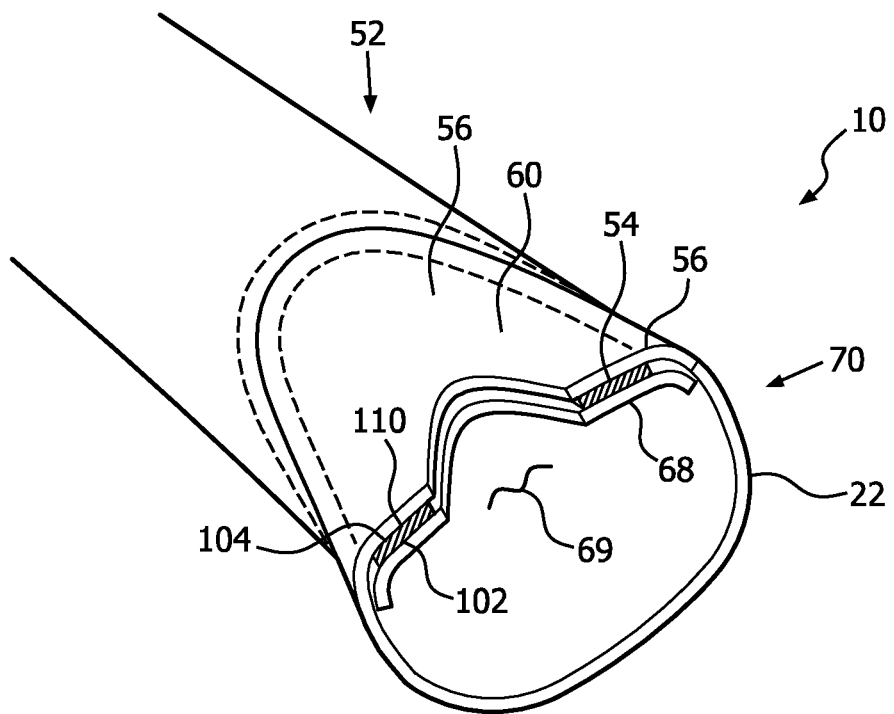
FIG. 8 is a cross-sectional view of cradle style sealing cushion taken along lines A-A of FIG. 6.
Figure 9:
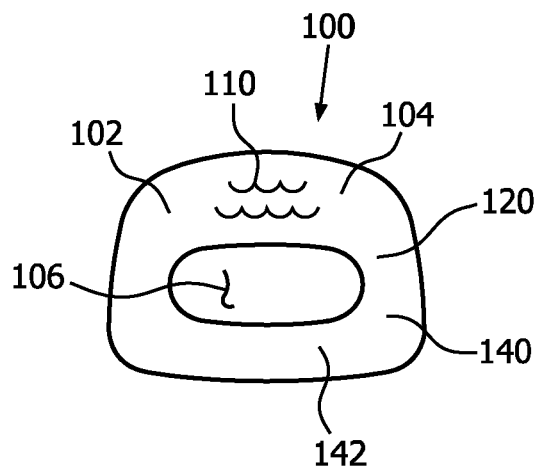
FIG. 9 is a top view of one embodiment of a custom cushion support assembly.
Figure 10:
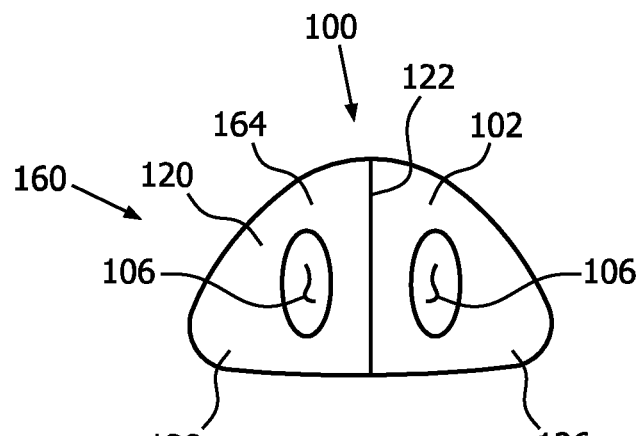
FIG. 10 is a top view of another embodiment of a custom cushion support assembly.
Figure 11:
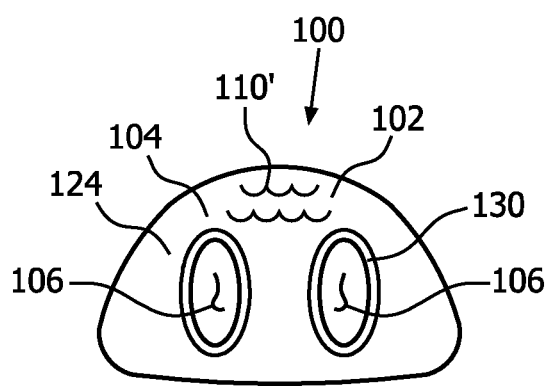
FIG. 11 is a top view of another embodiment of a custom cushion support assembly.
Figure 12:
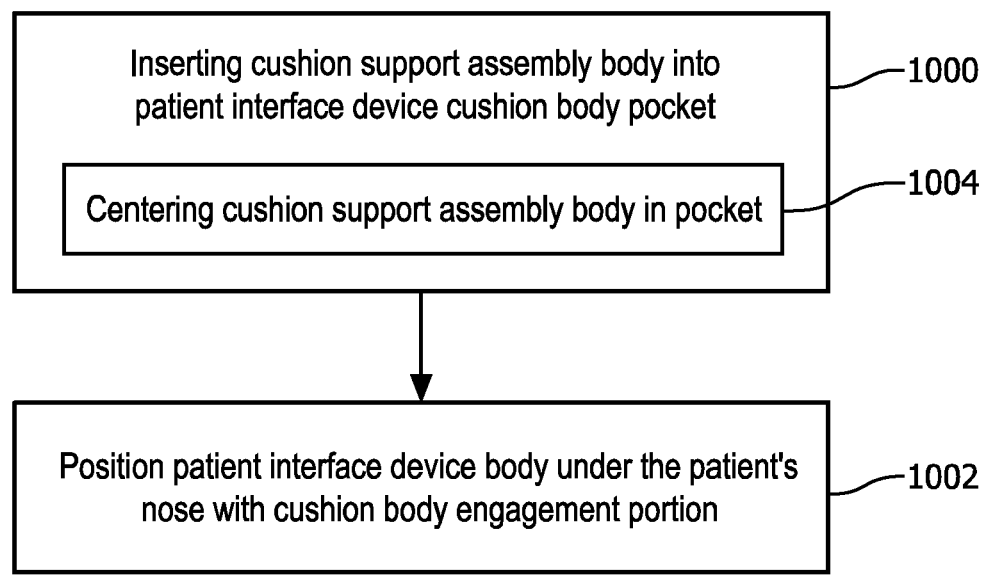
FIG. 12 is a flowchart of the disclosed method.

FIG. 2 is a front isometric view, FIG. 3 is a front elevation view, FIG. 4 is a side elevation view and FIG. 5 is a rear elevation view of cradle style patient interface device 10 according to an exemplary embodiment of the present invention. In the exemplary embodiment, cradle style patient interface device 10 is of a soft, flexible, cushiony material, such as, without limitation, silicone rubber, an appropriately soft thermoplastic elastomer, a fabric, or any combination of such materials. In an exemplary embodiment, cradle style patient interface device 10 is a unitary body. Cradle style patient interface device 10, however, may be made of separate components that are coupled to one another by suitable means.

Cradle style patient interface device 10 includes a body 22 (which may be identified hereinafter as "patient interface device body" 22) defining an internal chamber 23, a first port portion 24A provided on and extending from a first side of body 22, and a second port portion 24B provided on and extending from a second, opposite side of body 22. First port portion 24A and second port portion 24B are fluidly coupled to the body chamber 23. First port portion 24A includes a first opening 26A and is structured to be fluidly coupled to first arm 14A, while second port portion 24B includes a second opening 26B and is structured to be fluidly coupled to second arm 14B.

Patient interface device body 22 includes a sidewall 27. The portions of patient interface device body sidewall 27 include a front side 28 that is a front wall 29, a rear side 30 opposite front side 28 and which is rear wall 31, and, an upper side 32 which is an upper wall 33. In an exemplary embodiment, a number of exhaust holes 34 are provided in front wall 29 and act as an exhaust port for patient interface device 8. Alternatively, an exhaust port in the form of a semi-permeable porous material, such as a woven fabric, may be provided in place of exhaust holes 34. Patient interface device body 22 also includes a bottom wall 36 opposite upper wall 33.

Patient interface device body sidewall upper side 32 includes, i.e. defines, a number of passages 40. In an exemplary embodiment, patient interface device body sidewall upper side 32 includes a single passage 40. In this embodiment, the single patient interface device body sidewall upper side passage 40 has a cross-sectional area that is larger than the area of an average human's sub-nasal area. In an exemplary embodiment, patient interface device body 22 also includes a nose strap 48. Nose strap 48 is structured to extend over the tip of the patient's nose.

Cradle style patient interface device 10 further includes a cushion 50. In an exemplary embodiment, cushion 50 includes a resilient body 52. Further, in an exemplary embodiment, cushion body 52 is a silicone 54 backed fabric 56. That is, a fabric 56, such as, but not limited to, a poly spandex knit, is coupled, directly coupled, or fixed to a layer of silicone 54. In an exemplary embodiment, cushion body 52 has a hardness of between about 5-20 sHa, or about 10 sHa. Cushion body 52 includes an engagement portion 60 structured to engage the patent's sub-nasal area. That is, cushion body 52 is disposed on patient interface device body sidewall upper side 32 with fabric 56 outside chamber 23. As used herein, "disposed on" means coupled, directly coupled, fixed or unitary with. Thus, cushion body fabric 56 is exposed and generally faces generally upward. Cushion body fabric 56 may also extend over a portion of patient interface device body sidewall rear side 30. In this configuration, a portion of cushion body fabric 56 defines cushion body engagement portion 60.

Cushion body engagement portion 60 includes, i.e. defines, a number of passages 62. In one exemplary embodiment, cushion body engagement portion 60 defines a single passage 62. In this embodiment, cushion body engagement portion 60 is structured to engage a patient's peripheral sub-nasal area. In another embodiment, cushion body engagement portion 60 defines a two passages 62. In this embodiment, cushion body engagement portion 60 is structured to engage a patient's full sub-nasal area. Further, it is understood that in this embodiment, cushion body engagement portion passages 62 are generally configured to align with a patient's flares.

Further, cushion 50 includes an inner resilient body 68 which, as described below, is an inner layer of a pocket 70. Accordingly, cushion inner resilient body 68 is hereinafter identified as "inner resilient layer" 68. In an exemplary embodiment, inner resilient layer 68 includes a single passage 69. In another exemplary embodiment, inner resilient layer 68 includes a two passages 69. In an alternate embodiment, not shown, an inner layer is not substantially resilient.

Inner resilient layer 68 and cushion body 52 define a pocket 70. As used herein, pocket 70 is identified as "patient interface device cushion body pocket" 70. In this configuration, and in an exemplary embodiment, patient interface device cushion body pocket 70 is disposed under cushion body engagement portion 60. That is, when in use, cushion body engagement portion 60 is under the patient's nose and patient interface device cushion body pocket 70 is disposed under cushion body engagement portion 60.

Cradle style patient interface device 10 further includes a custom cushion support assembly 100. As used herein, a "custom cushion support assembly" is structured to fit a specific patient. That is, a patient's face is measured, e.g. scanned, and relevant dimensions are recorded. The patient's dimensions are then used to create a cushion support assembly body upper surface custom contour 110, as described below. Thus, a generic cushion support is not, as used herein, a "custom cushion support assembly." Stated alternately, if a cushion support is not structured to correspond to a specific patient, it is not a "custom cushion support assembly." Further, as used herein, a generic cushion support assembly is structured to, and can only, provide a generally continuous seal between cushion body engagement portion 60 and a specific patient's sub-nasal area, full sub-nasal area, peripheral sub-nasal area, and/or inner sub-nasal area. A custom cushion support assembly 100 is structured to, and does, provide a more complete seal between cushion body engagement portion 60 and a specific patient's sub-nasal area, full sub-nasal area, peripheral sub-nasal area, and/or inner sub-nasal area.

Custom cushion support assembly 100 includes a body 102. Custom cushion support assembly body 102 includes an upper surface 104 and defines a number of passages 106. Custom cushion support assembly body upper surface 104 includes a custom contour 110. As used herein, a "custom contour" 110 is a surface contour created to correspond to a specific patient's sub-nasal area, full sub-nasal area, peripheral sub-nasal area, and/or inner sub-nasal area. In an exemplary embodiment, custom contour 110 corresponds to, or substantially corresponds, to a specific patient's sub-nasal area, full sub-nasal area, peripheral sub-nasal area, and/or inner sub-nasal area. In another exemplary embodiment, custom contour 110 is an exaggerated custom contour 110'.

As used herein, an "exaggerated custom contour" 110' is a surface contour that does not itself correspond, or substantially correspond, to a specific patient's sub-nasal area, full sub-nasal area, peripheral sub-nasal area, and/or inner sub-nasal area, but which supports another component so that the other component corresponds, or substantially corresponds, to a specific patient's sub-nasal area, full sub-nasal area, peripheral sub-nasal area, and/or inner sub-nasal area. That is, resilient components, such as, but not limited to fabric and/or silicone backed fabric, drape in a predictable manner. Thus, a component with an exaggerated custom contour allows a resilient component to drape, (that is, as used herein, "to cover in a predictable manner") over custom cushion support assembly body 102 so that the fabric forms a surface that corresponds, or substantially corresponds, to a specific patient's sub-nasal area, full sub-nasal area, peripheral sub-nasal area, and/or inner sub-nasal area.

In an exemplary embodiment, custom cushion support assembly body 102 is one of a substantially rigid body 120, substantially rigid body 120 including a transverse hinge 122, or a substantially semi-rigid body 124. A substantially rigid body 120 has a hardness of greater than 100 sHa. In an exemplary embodiment, a substantially rigid body 120 is made from a rigid 3D printed material such as, but not limited to a resin material or an extruded thermoplastic.

A substantially rigid body 120 including a transverse hinge 122 is similar to a substantially rigid body 120 but includes a hinge 122, such as but not limited to a living hinge, disposed between a right lateral portion 126 and a left lateral portion 128 of substantially rigid body 120.

A substantially semi-rigid body 124 has a hardness of between about 20 and 60 sHa, or about 40 sHa. In an exemplary embodiment, a substantially semi-rigid body 124 is made from a material such as, but not limited to, silicone.

In one exemplary embodiment, custom cushion support assembly body 102 defines a single passage 106. In this embodiment, custom cushion support assembly body 102 is structured to support a cushion body engagement portion 60 that engages a patient's peripheral sub-nasal area. In another embodiment, custom cushion support assembly body 102 defines two passages 106. In this embodiment, custom cushion support assembly body 102 is structured to support a cushion body engagement portion 60 that engages a patient's full sub-nasal area. Further, it is understood that in this embodiment, custom cushion support assembly body passages 106 are generally configured to align with a patient's nares.

In an exemplary embodiment, custom cushion support assembly body 102 is generally smooth. That is, custom cushion support assembly body custom contour 110 corresponds, or substantially corresponds, to a specific patient's sub-nasal area, full sub-nasal area, peripheral sub-nasal area, and/or inner sub-nasal area, but does not include any constructs that deviate from a generally smooth surface. In another exemplary embodiment, custom cushion support assembly body 102 includes a number of collars 130. Collars 130 extend about, i.e. encircle, custom cushion support assembly body passages 106. Collars 130 extend generally perpendicular to custom cushion support assembly body upper surface 104. Collars 130 assist in deforming cushion body engagement portion 60 so that cushion body engagement portion 60 engages a patient's sub-inner sub-nasal area.

Custom cushion support assembly body 102 is one of a custom size or a generic size. Similarly, patient interface device cushion body pocket 70 is one of a custom size or a generic size. That is, as used herein, a custom cushion support assembly body 102 of a "custom size" is sized based upon a patient's face measured dimensions. Further, as used herein, a "generic size" is a pre-selected size that is not based upon any particular patient's face measured dimensions. A custom cushion support assembly body 102 of a custom size is structured to fit into a patient interface device cushion body pocket 70 of either a custom size or a generic size. A custom cushion support assembly body 102 of a generic size is structured to fit into a patient interface device cushion body pocket 70 of a generic size.

That is, cushion support assembly body 102 further includes a cushion body engagement support portion 140 and a peripheral portion 142. Custom cushion support assembly body upper surface custom contour 110 is disposed on cushion support assembly body cushion body engagement support portion 140. Custom cushion support assembly body upper surface custom contour 110 is structured for use with a specific patient. Cushion support assembly body peripheral portion 142 is, in one exemplary embodiment, also structured for use with a specific patient, i.e. corresponds to a specific patient's sub-nasal area, full sub-nasal area, peripheral sub-nasal area, and/or inner sub-nasal area. This embodiment is a cushion support assembly body 102 of a custom size. Such a cushion support assembly body 102 of a custom size is, in an exemplary embodiment, made by 3D printing individual cushion support assembly bodies 102.

In another embodiment, custom cushion support assembly body upper surface custom contour 110 is again disposed on cushion support assembly body cushion body engagement support portion 140. In this embodiment, however, cushion support assembly body peripheral portion 142 is a generic size. Thus, for example, a number of cushion support assembly bodies 102 may be manufactured and individualized by disposing custom cushion support assembly body upper surface custom contour 110 on cushion support assembly bodies 102 of a generic size.

Further, cushion support assembly body 102 and/or patient interface device cushion body pocket 70 includes an alignment device 160 structured to center cushion support assembly body 102 within patient interface device cushion body pocket 70. In an exemplary embodiment, alignment device 160 is the configuration/shape of cushion support assembly body 102 and patient interface device cushion body pocket 70. As shown, in an exemplary embodiment, cushion support assembly body 102 and patient interface device cushion body pocket 70 have a trapezoidal shape. Further, in an exemplary embodiment, cushion support assembly body 102 is sized to fit snugly within patient interface device cushion body pocket 70. In this configuration, cushion support assembly body 102 is aligned with patient interface device cushion body pocket 70 when inserted.

As indicated above, cradle style patient interface device 10 is assembled by disposing cushion support assembly body 102 in patient interface device cushion body pocket 70. When cushion support assembly body 102 is disposed in patient interface device cushion body pocket 70, cushion body engagement portion 60 deforms from a generic contour and becomes a custom contour. Further, in this configuration, patient interface device body sidewall upper side passage 40, cushion body engagement portion passage 62, and inner resilient layer passage 69 are aligned. That is, passages 40, 62, 69 are in fluid communication with each other along a common axis or axes. Further, when cushion support assembly body 102 is disposed in patient interface device cushion body pocket 70, cushion support assembly body peripheral portion 142 engages pocket 70.

Accordingly, a method of using a patient interface device 10 structured to engage a patient's sub-nasal area includes inserting 1000 cushion support assembly body 102 into patient interface device cushion body pocket 70, and, positioning 1002 patient interface device body 22 under the patient's nose with cushion body engagement portion 60 in corresponding engagement with the patient's sub-nasal area. As used herein, "corresponding engagement" means that a number of surfaces having a corresponding shape engage each other with corresponding portions thereof in engagement. It is noted that straps 18 are used to draw cradle style patient interface device 10 into engagement with patient's face, as is known. Further, inserting 1000 cushion support assembly body 102 into patient interface device cushion body pocket 70 includes centering 1004 cushion support assembly body 22 in pocket 70.

In the claims, any reference signs placed between parentheses shall not be construed as limiting the claim. The word "comprising" or "including" does not exclude the presence of elements or steps other than those listed in a claim. In a device claim, enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device structured to engage a patient's sub-nasal area, the patient interface device comprising:
    a unitary patient interface device body including a sidewall defining a chamber, the sidewall including a front wall, a rear wall, a bottom wall and an upper wall, the upper wall including a cushion body structured to engage the patient's sub-nasal area, the cushion body including a deformable engagement portion defining a first passage and an inner resilient layer defining a second passage aligned with the first passage along a common axis, wherein the engagement portion is spaced from inner resilient layer and the engagement portion and the inner resilient layer form a pocket;
    a custom cushion support assembly body separate and distinct from the unitary patient interface device body and received within the pocket between the engagement portion and the inner resilient layer, the custom cushion support assembly body including an upper surface including a custom contour having a shape that corresponds to dimensions measured from the patient's face, the custom cushion support assembly body defining a third passage aligned with the first passage and the second passage along the common axis;

wherein the custom contour is structured to deform the engagement portion to correspond to the patient's full sub-nasal area.

2. The patient interface device of claim 1, wherein the custom cushion support assembly body upper surface includes a collar encircling the third passage and extending generally perpendicular to the upper surface of the custom cushion support assembly body.

3. The patient interface device of claim 1, wherein the custom cushion support assembly body is one of a substantially rigid body, a substantially rigid body including a transverse hinge, or a substantially semi-rigid body.

4. The patient interface device of claim 1, wherein the cushion body has a hardness of between 5-20 sHa and the custom cushion support assembly body has a hardness of between 20 and 60 sHa.

5. The patient interface device of claim 4, wherein the cushion body has a hardness of 10 sHa and the custom cushion support assembly body has a hardness of 40 sHa.

6. The patient interface device of claim 1, further comprising a fabric layer provided directly on a top surface of the engagement portion, the fabric layer being structured to directly engage a patient's sub-nasal area.

7. The patient interface device of claim 1, wherein:
the unitary patient interface device body includes a first lateral port and a second lateral port; and
the patient interface device body first lateral port and the patient interface device body second lateral port are in fluid communication with the patient interface device body chamber.

8. The patient interface device of claim 1, wherein the unitary patient interface device body includes a nose strap.

9. A method of using a patient interface device structured to engage a patient's sub-nasal area, the patient interface device including a unitary patient interface device body including a sidewall defining a chamber, the sidewall including a front wall, a rear wall, a bottom wall and an upper wall, the upper wall including a cushion body structured to engage the patient's sub-nasal area, the cushion body including a deformable engagement portion defining a first passage and an inner resilient layer defining a second passage aligned with the first passage along a common axis, wherein the engagement portion is spaced from inner resilient layer and the engagement portion and the inner resilient layer form a pocket; and a custom cushion support assembly body separate and distinct from the unitary patient interface device body and structured to be received within the pocket between the engagement portion and the inner resilient layer, the custom cushion support assembly body including an upper surface including a custom contour having a shape that corresponds to dimensions measured from the patient's face, the custom cushion support assembly body defining a third passage aligned with the first passage and the second passage along the common axis; the method comprising:
inserting the custom cushion support assembly body into the pocket, wherein the custom contour deforms the engagement portion to correspond to the patient's full sub-nasal area; and
positioning the patient interface device body under the patient's nose with the cushion body engagement portion in corresponding engagement with the patient's full sub-nasal area.

10. The method of claim 9, wherein inserting the custom cushion support assembly body into the patient interface device cushion body pocket includes centering the custom cushion support assembly body in the pocket.

* * * * *